United States Patent
Schad

[11] Patent Number: 5,935,537
[45] Date of Patent: Aug. 10, 1999

[54] APPARATUS FOR CLEANSING AND/OR DISINFECTING SURGICAL INSTRUMENTS

[76] Inventor: Karl Schad, Hauptstrasse 28, D-78600 Kolbingen, Germany

[21] Appl. No.: 08/860,285
[22] PCT Filed: Mar. 27, 1996
[86] PCT No.: PCT/EP96/01333
 § 371 Date: Dec. 8, 1997
 § 102(e) Date: Dec. 8, 1997
[87] PCT Pub. No.: WO96/30058
 PCT Pub. Date: Oct. 3, 1996

[30] Foreign Application Priority Data

Mar. 28, 1995 [DE] Germany ............................ 195 11 037

[51] Int. Cl.[6] ................................ A61L 2/18; A61L 2/06; B08B 3/02
[52] U.S. Cl. ............................................. 422/300; 134/144
[58] Field of Search ...................................... 422/297, 300, 422/26; 134/107, 137, 149, 151, 153, 157, 144

[56] References Cited

U.S. PATENT DOCUMENTS

| 5,090,433 | 2/1992 | Kamaga ............................. 134/169 C |
| 5,279,799 | 1/1994 | Moser ................................. 422/300 X |
| 5,533,539 | 7/1996 | Sutter et al. ....................... 422/300 X |
| 5,554,228 | 9/1996 | Giordano et al. ................ 134/22.11 X |
| 5,758,675 | 6/1998 | Scheyer ................................... 134/148 |

Primary Examiner—Elizabeth McKane
Attorney, Agent, or Firm—Bachman & LaPointe, P. C.

[57] ABSTRACT

An apparatus for cleansing and disinfecting surgical instruments is disclosed wherein the apparatus includes a cleansing chamber for containing the instrument while proximate at least two nozzles for directing fluids onto the instrument. The nozzles and the instrument are simultaneously oscillated by separate rotary drives.

16 Claims, 2 Drawing Sheets

APPARATUS FOR CLEANSING AND/OR DISINFECTING SURGICAL INSTRUMENTS

BACKGROUND OF THE INVENTION

The present invention relates to an apparatus for cleansing and/or disinfecting surgical instruments, and to a method of doing this.

Surgical instruments are known in many shapes and embodiments and are available on the market. Problems arise today, in particular due to the increased demand for hygiene. It is known that diseases are transmitted by unclean instruments, which is absolutely undesired, particularly in view of the danger of transmitting hepatitis and AIDS. Therefore, it is required today that surgical instruments be cleaned extremely thoroughly. This applies, in particular, to those instruments which consist of many individual parts which become dirty upon the use of the instrument. Generally such parts are also located at difficultly accessible places, so that a simple rinsing with disinfecting liquid or the like is not sufficient. There must be absolute assurance that corresponding bacteria, viruses and other organisms or pathogens are killed.

This, however, applies, in particular, also to instruments which are inserted into the body of the patient. They include, for instance, biopsy forceps, instruments for minimal invasive surgery, arthroscopy, endoscopy, etc. The enumeration can be continued at length.

The object of the present invention is to develop an apparatus and a method of the above-mentioned type which satisfy these increased hygienic requirements.

SUMMARY OF THE INVENTION

In order to achieve this object, the surgical instrument is introduced into a cleansing chamber and is associated therein with at least one nozzle for spraying it with hot steam and/or hot air. The presence of two nozzles is preferred.

Bacteria, viruses and other pathogens can exist only at a given temperature. If this temperature is changed, the bacteria, viruses and other pathogens are also killed. In other words, the transmission of disease is basically avoided. The action of hot steam and/or hot air has the advantage that both of these fluids can penetrate deep into a surgical instrument and, in particular, also reach places which are generally not accessible to a cleansing liquid. Furthermore, by the action of hot steam or air the metal of the surgical instrument is also heated insofar as it consists of metal, as is the case at least for the jaws of the instrument, so that this heat is also transmitted to inaccessible places and the germs there are destroyed.

In order to produce steam or dry hot air, a heating device is arranged in front of the nozzles. As a rule, both water and air can be introduced into a reservoir in order to heat it. When necessary, steam or hot air is then removed from the corresponding reservoir. Connection to an external water network is also possible.

The control of the removal of hot steam or hot air is effected via a valve device which is preferably arranged together with the other operative elements within an operating chamber, said chamber being separated by a partition from the cleansing chamber. In this way a single unit which can be easily transported and handled is obtained. An improvement in the cleansing or disinfecting of the surgical instrument is furthermore obtained in the manner that the instrument is turned with respect to the nozzles or that the nozzles are turned with respect to the instrument. In this way, the steam or dry air can reach the most different points of the surgical instrument. One embodiment of a simple turning device consists of a rotary disk in which the surgical instrument is seated. The surgical instrument can possibly also be surrounded here by a holder which permits the adaptation of the rotary disk to surgical instruments of different shape.

The rotary disk is then connected to a drive. A rotary movement is transmitted to outer toothing on the rotary disk, for instance, by the drive via a gear. Many embodiments can be thought of here, all of which fall within the scope of the invention.

In an improved embodiment of the invention, the apparatus and the method of the invention are directed at instruments which have at least one tubular shaft on which a jaw is arranged. It is important here that this tubular shaft be subjected to particularly thorough cleansing and disinfection since it, in particular, permits the penetration of tissue fluid, blood, etc. These instruments comprise, for instance, the biopsy forceps described above, etc.

In this case, the jaw is acted on, in accordance with the invention, by the hot steam and then dried at a later time. For the cleansing and disinfecting of the inside of the tubular shaft and also of the inner joints of the jaw, etc., the tubular shaft, however, should be connected by a tube to a tank for disinfection liquid. The tubular shaft can then be rinsed with disinfection liquid.

The connection between tube and disinfection tank is preferably also produced by the valve device described above, so that here switching can be effected as desired. It is now also possible, before rinsing with disinfection liquid, to flush the tube, which may, for instance, be part of the surgical instrument, with water of a pressure of about 8 bar. After the disinfecting with the disinfection liquid, the disinfection liquid is blown out, preferably by hot air.

Since in the apparatus of the invention, fluids, whether water, steam or air or else disinfection liquid, are placed under pressure, one or more pumps are furthermore integrated in the operative part of the apparatus. They are also connected to the valve device so that they can be placed in operation as needed.

By the apparatus in accordance with the present invention, the cleansing and disinfecting of surgical instruments is automated, facilitated, and substantially improved. The apparatus operates on basis of programs, similar to a washing machine, depending on the surgical instrument in question and the requirements as to the cleansing and disinfecting.

BRIEF DESCRIPTION OF THE DRAWINGS

Other advantages, features, and details of the invention will become evident from the following description of embodiments, read with reference to the drawing, in which.

DETAILED DESCRIPTION

Figure 1:
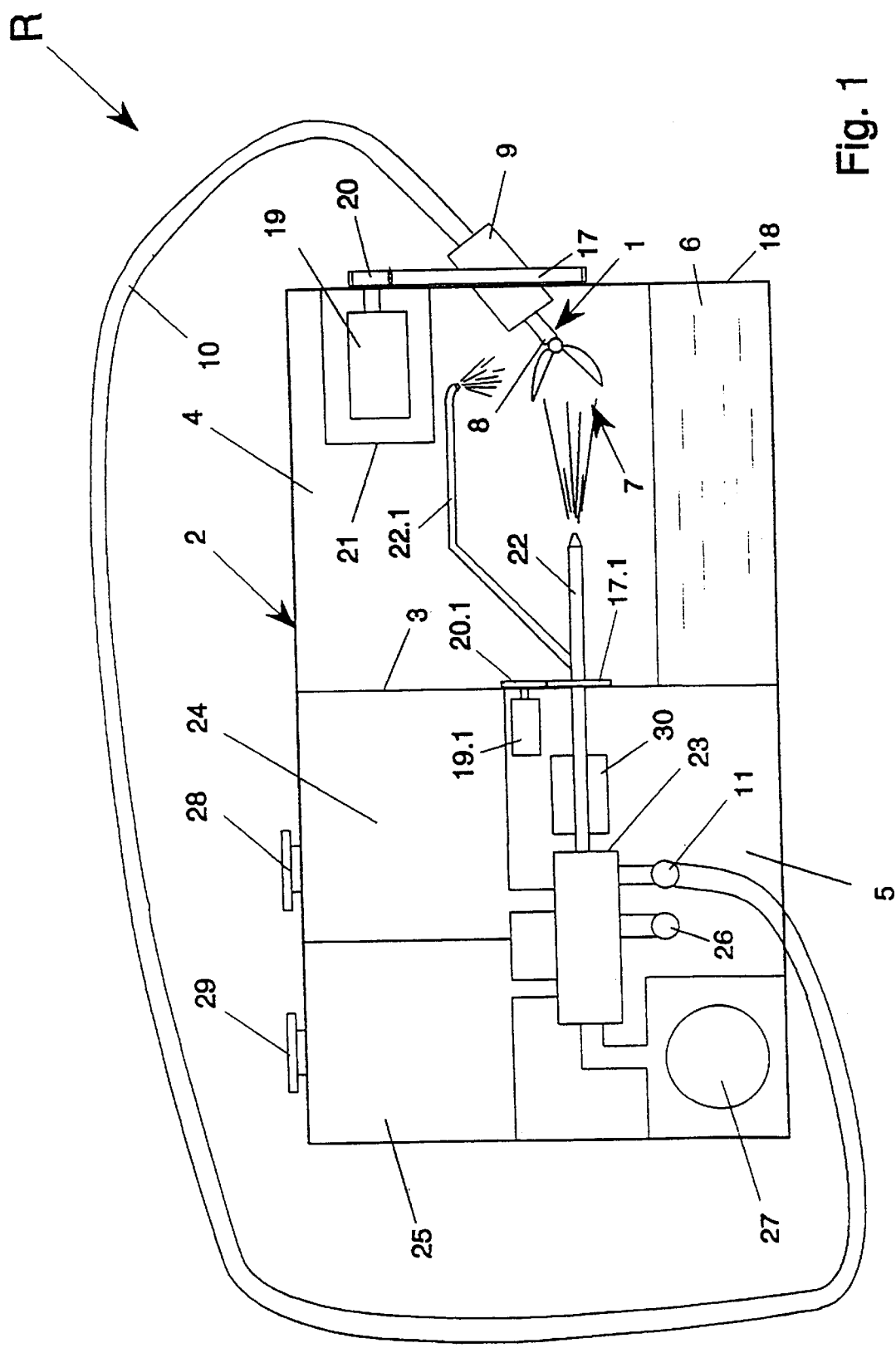
FIG. 1 is a diagrammatic front view of an apparatus in accordance with the invention for the cleansing and disinfecting of surgical instruments.

The apparatus R of the invention for the cleansing and disinfecting of surgical instruments 1, particularly of biopsy forceps, has a housing 2. This housing 2 is divided by a partition 3 into a cleansing chamber 4 and an operative chamber 5. The cleansing chamber 4 also includes a receiving trough 6 for the collecting of condensed steam or disinfection liquid.

The surgical instrument 1 has a jaw 7 in a tubular shaft 8. This tubular shaft is embedded in a holder 9 and on the other side has a flexible tube 10 which is connected by a connector 11 to the operative chamber 5. The tube 10 may consist of any flexible material, for instance plastic. There are instruments in which the tube 10 is part of the surgical instrument 1 so as, for instance, to conduct tissue specimens out of the body to a receiving container. There are also surgical instruments which do not have such a tube 10. In that case, the tube 10 is merely developed as a connecting line between the surgical instrument 1 and the connector 11.

Figure 2:
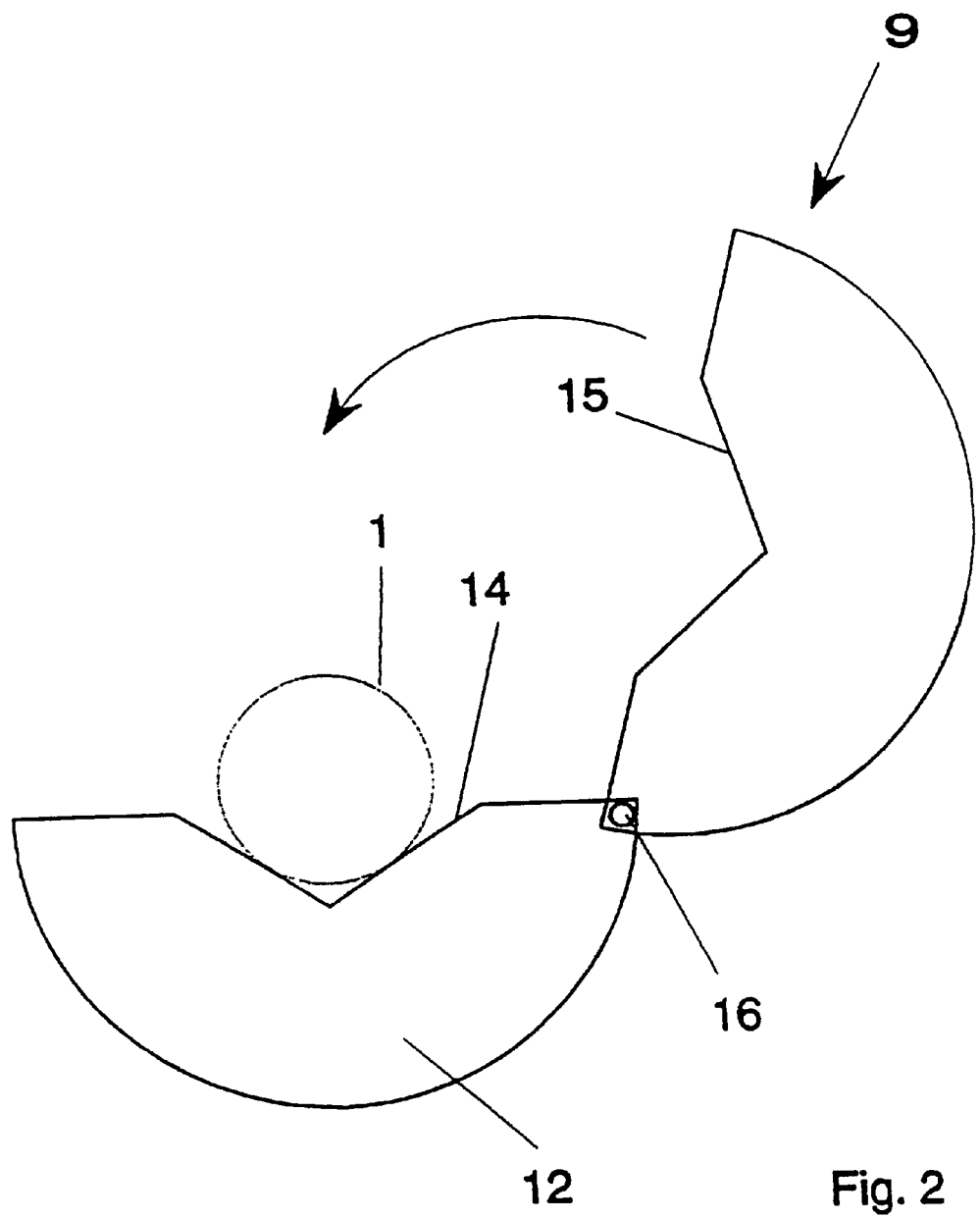
FIG. 2 is a cross section through an element of the apparatus of FIG. 1, along the line II—II.

The holder 9 consists, in accordance with FIG. 2, for the sake of simplicity of two half shells 12 and 13, each of which has a longitudinal groove 14 and 15 respectively to receive the surgical instrument 1. The two half shells 12 and 13 are connected to each other by a joint 16. The longitudinal grooves 14 and 15 preferably are of wedge shape so that they can receive surgical instruments 1 with tubular shafts of different diameter. Furthermore, it is also possible to line the longitudinal grooves 14 and 15 with elastic material so as to obtain a better gripping of surgical instruments 1 having tubular shafts of different diameter.

In position of use (see FIG. 1), the holder 9 is inserted in a rotary disk 17 which is arranged for rotation on an outer wall 18 of the housing 2. In this connection, the rotary disk 17 is connected to a drive 19 which can turn the rotary disk 17. For the sake of simplicity, a connection between the drive 19 and the rotary disk 17 is produced by a gear 20 which engages into an external toothing on the rotary disk 17. In the present embodiment, the drive 19 is within the cleansing chamber 4 and is therefore covered by a cover 21.

Within the cleansing chamber 4 two nozzles 22.1 and 22.2 are associated with the surgical instrument 1 and, in particular, with the jaw 7, through which nozzles the jaw 7 can be acted on by steam, disinfection liquid and/or air. These nozzles can be made rotatable by similar means (17.1, 19.1, 20.1) as the holder 9.

Within the operative chamber 5, the nozzles 22 are connected to a valve device 23, which has been indicated only schematically. To this valve device 23 there are furthermore connected a water tank 24, a tank 25 for the disinfection liquid, a compressed-air connection 26 to the outside or to an integrated air generator, and a pump 27. The valve device 22 can connect both the nozzles 22 and the connector 13, via the tube 10, to the surgical instrument 1, the water tank 24, the disinfection tank 25 or the compressed air connector 26. Within the valve device 23 the necessary pressure is maintained by the pump 27.

Water tank 24 and disinfection tank 25 are closed by suitable covers 28 and 29.

The manner of operation of the present invention is as follows:

For its cleansing and disinfection the surgical instrument 1 is placed in the holder 9. In this connection, the tubular shaft 8 lies in the corresponding longitudinal grooves 14 and 15. If the surgical instrument 1 does not have a flexible tube 10, it is connected at its rear to the tube 10 of the apparatus R. Otherwise, the tube 10 is fastened to the connector 11.

The holder 9 is now pushed into the rotary disk 17, in which the holder 9 is held in form-locked and/or force-locked manner. For example, the rotary disk 17 can have a recess which is lined with a rubberlike material. This rubberlike material then closely surrounds the holder 9, so that the holder 9 can be turned with respect to the rotary disk 17 only by the application of increased force.

In this position of use, the jaw 7 of the surgical instrument 1 is close to the nozzles 22. The jaw 7 is now acted on by hot steam of about 120° C. from the nozzles 22. During this treatment with steam, the surgical instrument 1 should be turned. For this purpose, the drive 19 is actuated, it turning the rotary disk 17 preferably twice to the right and then twice to the left. In this way, the jaw is acted on with steam on all sides. Thus the jaw and, in particular, the joint parts are effectively cleansed and disinfected.

The valve device 23 then connects the disinfection tank 25 with the connector 11 so that the entire surgical instrument 1 can be rinsed and cleansed with disinfection liquid via the tube 10.

After the rinsing with disinfection liquid, one should wait awhile in order to allow the disinfection liquid to act on all regions of the surgical instrument 1. The valve device 23 now connects the connector 11 to the compressed air connector 26. The surgical instrument 1 is blown out with compressed air through the tube 10 so that no disinfection liquid remains any longer in the surgical instrument 1. A prior rinsing with water is also possible.

Thereupon the compressed air connector 26 is connected to the nozzles 22, a heating device 30 heating the air in front of the nozzles 22. In other words, the jaw 7 is now dried by hot air. During this also, the instrument 1 can again be turned.

It is self-evident that the entire cleansing and disinfecting process is to take place as fully automatically as possible, i.e. a suitable electronic circuit with automatic control is to be associated with the apparatus R. For the sake of simplicity this has been omitted in the drawings.

I claim:

1. An apparatus for cleansing and disinfecting surgical instruments, comprises:
    a housing;
    means for dividing the housing into an operative chamber and a cleansing chamber;
    at least two nozzles located in said cleansing chamber;
    a valve located in said operative chamber;
    conduit means connected between said valve and said at least two nozzles;
    cleansing and disinfecting medium source connected to said valve device;
    support means on said housing for receiving said surgical instrument and supporting same in said cleansing chamber proximate to said at least two nozzles;
    first drive means for selectively oscillating said at least two nozzles;
    second drive means for selectively oscillating said surgical instrument; and
    means for feeding said cleansing and disinfecting medium to said at least two nozzles and onto said surgical instrument while oscillating said at least two nozzles and said surgical instrument.

2. An apparatus according to claim 1 wherein a heating device is connected to said conduit means.

3. An apparatus according to claim 2 wherein said heating device is located in said operative chamber.

4. An apparatus according to claim 1 wherein said support means includes a holder which comprises two half shells which are connected to each other by a joint, each of said shells having a longitudinal groove to receive the surgical instrument.

5. An apparatus according to claim 4 wherein said holder is placed in a rotary disk which is connected via a gear to said second drive.

6. An apparatus according to claim 1 wherein said surgical instrument has a jaw on a tubular shaft which is connected by a tube to a connector in said operative chamber.

7. An apparatus according to claim 6 wherein said connector is connected to said cleansing and disinfecting medium source.

8. An apparatus according to claim 1 wherein at least one pump is connected to said valve.

9. An apparatus for cleansing and disinfecting surgical instruments, comprises:

a housing;

means for dividing the housing into an operative chamber and a cleansing chamber;

at least one nozzle located in said cleansing chamber;

a valve located in said operative chamber;

conduit means connected between said valve and said at least one nozzle;

cleansing and disinfecting medium source connected to said valve device;

support means on said housing for receiving said surgical instrument, wherein said surgical instrument has a jaw on a tubular shaft which is connected by a tube to a connector in said operative chamber and supporting said surgical instrument in said cleansing chamber proximate to said at least one nozzle;

drive means for selectively oscillating said surgical instrument; and means for feeding said cleansing and disinfecting medium to said at least one nozzle and onto said surgical instrument while oscillating said surgical instrument.

10. An apparatus according to claim 9 wherein a heating device is connected to said conduit means.

11. An apparatus according to claim 10 wherein said heating device is located in said operative chamber.

12. An apparatus according to claim 9 wherein said support means includes a holder which comprises two half shells which are connected to each other by a joint, each of said shells having a longitudinal groove to receive the surgical instrument.

13. An apparatus according to claim 12 wherein said holder is placed in a rotary disk which is connected via a gear to said second drive.

14. An apparatus according to claim 9 wherein said surgical instrument has a jaw on a tubular shaft which can be connected by a tube to a connector in said operative chamber.

15. An apparatus according to claim 14 wherein said connector is connected to said cleansing and disinfecting medium source.

16. An apparatus according to claim 9 wherein at least one pump is connected to said valve.

* * * * *